United States Patent
Panjabi et al.

(10) Patent No.: US 9,005,252 B2
(45) Date of Patent: *Apr. 14, 2015

(54) METHOD FOR STABILIZING A SPINE

(75) Inventors: Manohar M. Panjabi, Cancord, MA (US); Jens P. Timm, Carlsbad, CA (US); George Malcolmson, II, New Haven, CT (US)

(73) Assignees: Yale University, New Haven, CT (US); Rachiotek, LLC, Wellesly, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/409,605

(22) Filed: Mar. 1, 2012

(65) Prior Publication Data

US 2012/0165877 A1    Jun. 28, 2012

Related U.S. Application Data

(60) Continuation of application No. 13/089,878, filed on Apr. 19, 2011, now Pat. No. 8,500,781, and a division of application No. 11/159,471, filed on Jun. 23, 2005, now Pat. No. 7,931,675.

(60) Provisional application No. 60/581,716, filed on Jun. 23, 2004.

(51) Int. Cl.
    *A61B 17/70* (2006.01)

(52) U.S. Cl.
    CPC ......... *A61B 17/7028* (2013.01); *A61B 17/7007* (2013.01); *A61B 17/702* (2013.01); *A61B 17/7026* (2013.01); *A61B 17/7041* (2013.01); *A61B 17/7049* (2013.01)

(58) Field of Classification Search
    USPC .................................... 606/246, 250–279
    See application file for complete search history.

(56) References Cited

U.S. PATENT DOCUMENTS

| | | |
|---|---|---|
| 2,733,596 A | 2/1956 | Painter |
| 4,328,960 A | 5/1982 | Handke et al. |
| 4,352,514 A | 10/1982 | Orima |

(Continued)

FOREIGN PATENT DOCUMENTS

| | | |
|---|---|---|
| AU | 744241 | 7/1999 |
| CA | 2135838 | 5/1995 |

(Continued)

OTHER PUBLICATIONS

Panjabi, The Stabilizing System of the Spine, Part I. Function, Dysfunction, Adaptation, and Enhancement, Journal of Spinal Disorders, 1992, vol. 5, No. 4, pp. 383-389.

(Continued)

*Primary Examiner* — Mary Hoffman
(74) *Attorney, Agent, or Firm* — McCarter & English, LLP

(57) ABSTRACT

Spine stabilization devices, systems and methods are provided in which a single resilient member or spring is disposed on an elongate element that spans two attachment members attached to different spinal vertebrae. The elongate element passes through at least one of the two attachment members, permitting relative motion therebetween, and terminates in a stop or abutment. A second resilient member is disposed on the elongate element on an opposite side of the sliding attachment member, e.g., in an overhanging orientation. The two resilient members are capable of applying mutually opposing urging forces, and a compressive preload can be applied to one or both of the resilient members.

14 Claims, 13 Drawing Sheets

(56) References Cited

U.S. PATENT DOCUMENTS

| | | | |
|---|---|---|---|
| 4,558,852 A | 12/1985 | Steiner et al. | |
| 4,650,167 A | 3/1987 | Steiner et al. | |
| 4,743,260 A | 5/1988 | Burton | |
| 4,759,769 A | 7/1988 | Hedman et al. | |
| 5,010,879 A * | 4/1991 | Moriya et al. | 606/276 |
| 5,034,011 A | 7/1991 | Howland | |
| 5,174,551 A | 12/1992 | Mintgen | |
| 5,176,679 A * | 1/1993 | Lin | 606/272 |
| 5,180,393 A | 1/1993 | Commarmond | |
| 5,291,901 A | 3/1994 | Graf | |
| 5,329,933 A | 7/1994 | Graf | |
| 5,375,823 A | 12/1994 | Navas | |
| 5,415,661 A | 5/1995 | Holmes | |
| 5,423,816 A | 6/1995 | Lin | |
| 5,480,401 A | 1/1996 | Navas | |
| 5,501,684 A | 3/1996 | Schlapfer et al. | |
| 5,505,118 A | 4/1996 | Arnesen et al. | |
| 5,540,688 A | 7/1996 | Navas | |
| 5,562,660 A * | 10/1996 | Grob | 606/258 |
| 5,562,737 A | 10/1996 | Graf | |
| 5,653,680 A | 8/1997 | Cruz | |
| 5,672,175 A * | 9/1997 | Martin | 606/86 A |
| RE36,221 E | 6/1999 | Breard et al. | |
| 5,961,516 A | 10/1999 | Graf | |
| 6,162,223 A | 12/2000 | Orsak et al. | |
| 6,176,860 B1 | 1/2001 | Howard | |
| 6,241,730 B1 | 6/2001 | Alby | |
| 6,267,764 B1 | 7/2001 | Elberg | |
| 6,293,949 B1 | 9/2001 | Justis et al. | |
| 6,375,681 B1 | 4/2002 | Truscott | |
| 6,402,750 B1 | 6/2002 | Atkinson et al. | |
| 6,419,706 B1 | 7/2002 | Graf | |
| 6,440,169 B1 | 8/2002 | Elberg et al. | |
| 6,508,818 B2 | 1/2003 | Steiner et al. | |
| 6,554,831 B1 | 4/2003 | Rivard et al. | |
| 6,645,207 B2 | 11/2003 | Dixon et al. | |
| 6,761,719 B2 | 7/2004 | Justis et al. | |
| 6,835,205 B2 | 12/2004 | Atkinson et al. | |
| 7,326,210 B2 * | 2/2008 | Jahng et al. | 606/86 A |
| 7,722,649 B2 * | 5/2010 | Biedermann et al. | 606/257 |
| 7,931,675 B2 * | 4/2011 | Panjabi et al. | 606/257 |
| 8,465,526 B2 * | 6/2013 | Friedrich et al. | 606/257 |
| 8,500,781 B2 | 8/2013 | Panjabi et al. | |
| 2002/0095154 A1 | 7/2002 | Atkinson et al. | |
| 2002/0151978 A1 | 10/2002 | Zacouto et al. | |
| 2003/0055427 A1 | 3/2003 | Fraf | |
| 2003/0109880 A1 | 3/2003 | Graf | |
| 2003/0171749 A1 | 9/2003 | Le Couedic et al. | |
| 2003/0220642 A1 | 11/2003 | Freudiger | |
| 2003/0220643 A1 | 11/2003 | Ferree | |
| 2004/0049189 A1 | 3/2004 | Le Couedic et al. | |
| 2004/0049190 A1 * | 3/2004 | Biedermann et al. | 606/61 |
| 2004/0082954 A1 | 4/2004 | Teitelbaum et al. | |
| 2004/0143264 A1 | 7/2004 | McAfee | |
| 2004/0147928 A1 | 7/2004 | Landry et al. | |
| 2004/0167523 A1 | 8/2004 | Jackson | |
| 2004/0267260 A1 | 12/2004 | Mack et al. | |
| 2005/0203519 A1 | 9/2005 | Harms et al. | |
| 2006/0036240 A1 * | 2/2006 | Colleran et al. | 606/61 |
| 2006/0247635 A1 * | 11/2006 | Gordon et al. | 606/61 |
| 2006/0264937 A1 | 11/2006 | White | |
| 2007/0016190 A1 | 1/2007 | Martinez et al. | |
| 2007/0213720 A1 * | 9/2007 | Gordon et al. | 606/61 |

FOREIGN PATENT DOCUMENTS

| | | |
|---|---|---|
| CA | 2213058 | 2/1998 |
| EP | 0516567 | 12/1992 |
| EP | 0534874 | 3/1993 |
| EP | 0576379 | 12/1993 |
| EP | 0611554 | 8/1994 |
| EP | 0821917 | 2/1998 |
| EP | 1039855 | 6/2004 |
| FR | 2676911 | 12/1992 |
| FR | 2681520 | 3/1993 |
| FR | 2692468 | 12/1993 |
| FR | 2694182 | 2/1994 |
| FR | 2071650 | 8/1994 |
| FR | 2701650 | 8/1994 |
| FR | 2701651 | 8/1994 |
| FR | 2751864 | 2/1998 |
| FR | 2772594 | 6/1999 |
| FR | 2775891 | 9/1999 |
| FR | 2794362 | 12/2000 |
| FR | 2799949 | 4/2001 |
| FR | 2801782 | 6/2001 |
| FR | 2803188 | 7/2001 |
| FR | 2809304 | 11/2001 |
| FR | 2810873 | 1/2002 |
| FR | 2812535 | 2/2002 |
| GB | 2382304 | 5/2003 |
| JP | 6-285100 | 10/1994 |
| JP | 7-289562 | 11/1995 |
| JP | 10-71157 | 3/1998 |
| JP | 10-277070 | 10/1998 |
| WO | 1999/32054 | 7/1999 |
| WO | 2001/39678 | 6/2001 |
| WO | 2001/45576 | 6/2001 |
| WO | 2001/49192 | 7/2001 |
| WO | 2002/00124 | 1/2002 |
| WO | 2002/102259 | 12/2002 |

OTHER PUBLICATIONS

Panjabi, The Stabilizing System of the Spine Part II. Neutral Zone and Instability Hypothesis, Journal of Spinal Disorders, 1992, vol. 5, No. 4, pp. 390-397.

PCT International Search Report dated Feb. 22, 2006.

* cited by examiner

DSS in Tension

DSS in Tension

Free-body diagram

METHOD FOR STABILIZING A SPINE

CROSS-REFERENCE TO RELATED APPLICATIONS

The present application claims priority benefit to a co-pending non-provisional application entitled "Method for Stabilizing a Spine," which was filed on Apr. 19, 2011 and assigned Ser. No. 12/089,878, and which claims priority benefit to a non-provisional patent application entitled "Dynamic Stabilization Device Including Overhanging Stabilizing Member," which was filed on Jun. 23, 2005 and assigned Ser. No. 11/159,471 (now U.S. Pat. No. 7,931,675). The foregoing non-provisional patent applications claim priority benefit to a provisional patent application entitled "Dynamic Spine Stabilizer," filed on Jun. 23, 2004 and assigned Ser. No. 60/581, 716. The entire content of the foregoing provisional patent application is incorporated by reference herein.

STATEMENT REGARDING FEDERALLY SPONSORED RESEARCH

This invention was made with government support under Grant No. AR045452 awarded by the National Institute of Health. The government has certain rights in the invention.

BACKGROUND OF THE DISCLOSURE

1. Technical Field

The present disclosure is directed to a dynamic stabilization device and system for spinal implantation and, more particularly, to a dynamic stabilization device and system that is adapted to be positioned/mounted relative to first and second laterally-spaced pedicle screws and that includes at least one dynamic stabilization member that is positioned beyond the region defined between the pedicle screws, e.g., in an "overhanging" orientation.

2. Background Art

Low back pain is one of the most expensive diseases afflicting industrialized societies. With the exception of the common cold, it accounts for more doctor visits than any other ailment. The spectrum of low back pain is wide, ranging from periods of intense disabling pain which resolve, to varying degrees of chronic pain. The conservative treatments available for lower back pain include: cold packs, physical therapy, narcotics, steroids and chiropractic maneuvers. Once a patient has exhausted all conservative therapy, the surgical options range from micro discectomy, a relatively minor procedure to relieve pressure on the nerve root and spinal cord, to fusion, which takes away spinal motion at the level of pain.

Each year, over 200,000 patients undergo lumbar fusion surgery in the United States. While fusion is effective about seventy percent of the time, there are consequences even to these successful procedures, including a reduced range of motion and an increased load transfer to adjacent levels of the spine, which accelerates degeneration at those levels. Further, a significant number of back-pain patients, estimated to exceed seven million in the U.S., simply endure chronic low-back pain, rather than risk procedures that may not be appropriate or effective in alleviating their symptoms.

New treatment modalities, collectively called motion preservation devices, are currently being developed to address these limitations. Some promising therapies are in the form of nucleus, disc or facet replacements. Other motion preservation devices provide dynamic internal stabilization of the injured and/or degenerated spine, without removing any spinal tissues. A major goal of this concept is the stabilization of the spine to prevent pain while preserving near normal spinal function. The primary difference in the two types of motion preservation devices is that replacement devices are utilized with the goal of replacing degenerated anatomical structures which facilitates motion while dynamic internal stabilization devices are utilized with the goal of stabilizing and controlling abnormal spinal motion.

Over ten years ago a hypothesis of low back pain was presented in which the spinal system was conceptualized as consisting of the spinal column (vertebrae, discs and ligaments), the muscles surrounding the spinal column, and a neuromuscular control unit which helps stabilize the spine during various activities of daily living. Panjabi M M. "The stabilizing system of the spine. Part I. Function, dysfunction, adaptation, and enhancement." *J Spinal Disord* 5 (4): 383-389, 1992a. A corollary of this hypothesis was that strong spinal muscles are needed when a spine is injured or degenerated. This was especially true while standing in neutral posture. Panjabi M M. "The stabilizing system of the spine. Part II. Neutral zone and instability hypothesis." *J Spinal Disord* 5 (4): 390-397, 1992b. In other words, a low-back patient needs to have sufficient well-coordinated muscle forces, strengthening and training the muscles where necessary, so they provide maximum protection while standing in neutral posture.

Dynamic stabilization (non-fusion) devices need certain functionality in order to assist the compromised (injured or degenerated with diminished mechanical integrity) spine of a back patient. Specifically, the devices must provide mechanical assistance to the compromised spine, especially in the neutral zone where it is needed most. The "neutral zone" refers to a region of low spinal stiffness or the toe-region of the Moment-Rotation curve of the spinal segment (see FIG. 1). Panjabi M M, Goel V K, Takata K. 1981 Volvo Award in Biomechanics. "Physiological Strains in Lumbar Spinal Ligaments, an in vitro Biomechanical Study." *Spine* 7 (3): 192-203, 1982. The neutral zone is commonly defined as the central part of the range of motion around the neutral posture where the soft tissues of the spine and the facet joints provide least resistance to spinal motion. This concept is nicely visualized on a load-displacement or moment-rotation curve of an intact and injured spine as shown in FIG. 1. Notice that the curves are non-linear; that is, the spine mechanical properties change with the amount of angulations and/or rotation. If we consider curves on the positive and negative sides to represent spinal behavior in flexion and extension respectively, then the slope of the curve at each point represents spinal stiffness. As seen in FIG. 1, the neutral zone is the low stiffness region of the range of motion.

Experiments have shown that after an injury of the spinal column or due to degeneration, neutral zones, as well as ranges of motion, increase (see FIG. 1). However, the neutral zone increases to a greater extent than does the range of motion, when described as a percentage of the corresponding intact values. This implies that the neutral zone is a better measure of spinal injury and instability than the range of motion. Clinical studies have also found that the range of motion increase does not correlate well with low back pain. Therefore, the unstable spine needs to be stabilized especially in the neutral zone. Dynamic internal stabilization devices must be flexible so as to move with the spine, thus allowing the disc, the facet joints, and the ligaments normal physiological motion and loads necessary for maintaining their nutritional well-being. The devices must also accommodate the different physical characteristics of individual patients and anatomies to achieve a desired posture for each individual patient.

With the foregoing in mind, those skilled in the art will understand that a need exists for a spinal stabilization device which overcomes the shortcoming of prior art devices. The present invention provides such an apparatus and method for spinal stabilization.

SUMMARY OF THE DISCLOSURE

The present disclosure provides advantageous apparatus and methods for stabilizing adjacent spinal vertebrae in spinal axial rotation and spinal lateral bending. The disclosed stabilization devices and systems are adapted to be disposed between laterally-spaced pedicle screws attached to the same spinal vertebra. The disclosed spinal stabilization devices/systems are advantageously adapted to include at least first and second stabilizing elements which function, according to exemplary embodiments, in concert for stabilization in spinal flexion and spinal extension. Thus, according to exemplary embodiments of the present disclosure, the spinal stabilization devices/systems provide stabilizing functionality with laterally-spaced pedicle screws, but in a manner that is not confined within the region defined between such laterally-spaced pedicle screws. Such spinal stabilization designs offer several clinical advantages, including a reduced spatial requirement between the laterally-spaced pedicle screws since a portion of the stabilization functionality is achieved through structures positioned beyond such laterally-spaced region, e.g., in an overhanging orientation relative to one of the laterally-spaced pedicle screws.

According to an exemplary embodiment of the present disclosure, a dynamic spine stabilization device/system is provided that is adapted to span adjacent spinal vertebrae. Attachment members are provided to mount/position the dynamic spine stabilization device/system with respect to laterally-spaced pedicle screws that are mounted into the adjacent spinal vertebrae. The attachment members of the spine stabilization device/system are generally coupled/mounted with respect to the laterally-spaced pedicle screws and are adapted to couple to the disclosed spinal stabilization device/system. Of note, the spinal stabilization device/system includes a dynamic element that is positioned between the first and second pedicle screws, and at least one additional dynamic element that is positioned beyond or external to the region defined by the laterally-spaced pedicle screws.

According to an exemplary embodiment of the present disclosure, first and second dynamic elements are associated with the disclosed dynamic stabilization device/system. A first dynamic element is positioned on a first side of an attachment member and a second dynamic element is positioned on the opposite side of such attachment member. Relative motion between the pedicle screws, which is based upon and responsive to spinal motion (i.e., in flexion or extension), is stabilized through the combined contributions of the first and second dynamic elements. Each dynamic element includes one or more components that contribute to the dynamic response thereof, e.g., one or more springs. According to exemplary embodiments, a pair of springs are associated with each of the dynamic elements, e.g., in a nested configuration. In a further exemplary embodiment, each of the dynamic elements includes a single spring, and the single springs are adapted to operate in concert to provide an advantageous stabilizing response to spinal motion.

According to other exemplary embodiments of the present disclosure, a dynamic stabilization device/system is provided in which an elongate rod/pin extends from both sides of an attachment member. The dynamic stabilization device/system may be equipped with one or more stops associated with the elongate rod/pin. First and second resilient members may be disposed on the pin (e.g., springs), the first resilient member being located in the region defined between the first attachment member and the second attachment member, and the second resilient member being located between either the first or the second attachment member and the stop. According to further exemplary embodiments of the present disclosure, a compressive preload may be established with respect to a first resilient member, a second resilient member, or both, to provide a desired stabilizing force profile, as described in greater detail herein.

Exemplary methods of use of the disclosed dynamic stabilization devices and systems are also provided in accordance with the present disclosure. The disclosed dynamic stabilization devices, systems and methods of use have a variety of applications and implementations, as will be readily apparent from the disclosure provided herein. Additional advantageous features and functionalities associated with the present disclosure will be apparent from the detailed description which follows, particularly when read in conjunction with the figures appended hereto.

BRIEF DESCRIPTION OF THE DRAWINGS

To assist those of ordinary skill in the art in making and using the disclosed spinal stabilization device/system, reference is made to the accompanying figures, wherein.

DESCRIPTION OF EXEMPLARY EMBODIMENTS

Exemplary embodiments of the disclosed dynamic stabilization system/device are presented herein. It should be understood, however, that the disclosed embodiments are merely exemplary of the present invention, which may be embodied in various forms. Therefore, the details disclosed herein are not to be interpreted as limiting, but merely as the basis for teaching one skilled in the art how to make and/or use the devices and systems of the present disclosure.

With reference to FIGS. 2, 3a-e and 4, a method and apparatus are disclosed for spinal stabilization. In accordance with a preferred embodiment of the present disclosure, the spinal stabilization method is achieved by securing an internal dynamic spine stabilization device 10 between adjacent vertebrae 12, 14 and providing mechanical assistance in the form of elastic resistance to the region of the spine to which the dynamic spine stabilization device 10 is attached. The elastic resistance is applied as a function of displacement such that greater mechanical assistance is provided while the spine is in its neutral zone and lesser mechanical assistance is provided while the spine bends beyond its neutral zone. Although the term elastic resistance is used throughout the body of the present specification, other forms of resistance may be employed without departing from the spirit or scope of the present disclosure.

Figure 2:
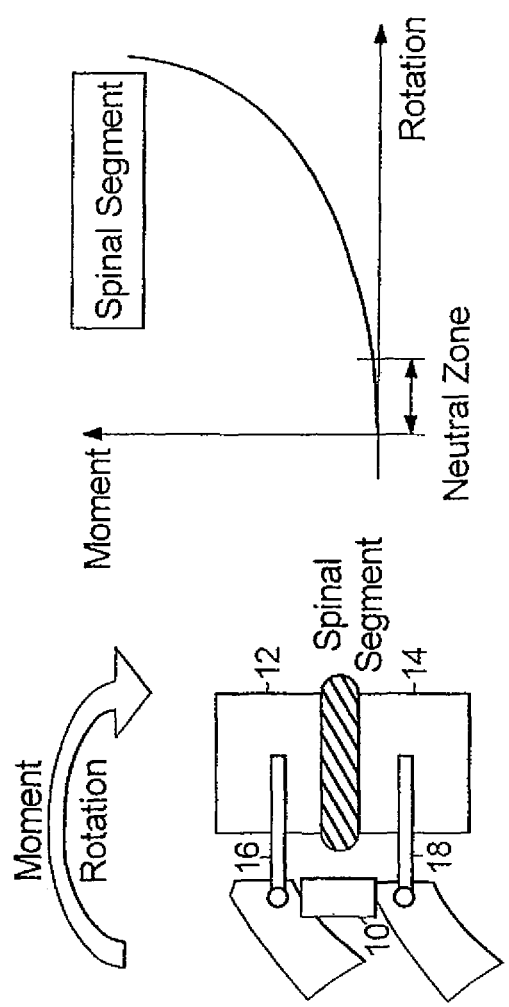
FIG. 2 is a schematic representation of a spinal segment in conjunction with a Moment-Rotation curve for a spinal segment, showing low spinal stiffness within the neutral zone.

As those skilled in the art will certainly appreciate, and as mentioned above, the "neutral zone" is understood to refer to a region of low spinal stiffness or the toe-region of the Moment-Rotation curve of the spinal segment (see FIG. 2). That is, the neutral zone may be considered to refer to a region of laxity around the neutral resting position of a spinal segment where there is minimal resistance to intervertebral motion. The range of the neutral zone is considered to be of major significance in determining spinal stability. Panjabi, M M. "The stabilizing system of the spine. Part II. Neutral zone and instability hypothesis." *J Spinal Disorders* 1992; 5(4): 390-397.

In fact, the inventor has previously described the load displacement curve associated with spinal stability through the use of a "ball in a bowl" analogy. According to this analogy, the shape of the bowl indicates spinal stability. A deeper bowl represents a more stable spine, while a more shallow bowl represents a less stable spine. The inventor previously hypothesized that for someone without spinal injury there is a normal neutral zone (that part of the range of motion where there is minimal resistance to intervertebral motion) with a normal range of motion, and in turn, no spinal pain. In this instance, the bowl is not too deep nor too shallow. However, when an injury occurs to an anatomical structure, the neutral zone of the spinal column increases and the ball moves freely over a larger distance. By this analogy, the bowl would be more shallow and the ball less stable, and consequently, pain results from this enlarged neutral zone.

In general, pedicle screws 16, 18 attach the dynamic spine stabilization device 10 to the vertebrae 12, 14 of the spine using well-tolerated and familiar surgical procedures known to those skilled in the art. In accordance with a preferred embodiment, and as those skilled in the art will certainly appreciate, a pair of opposed stabilization devices are commonly used to balance the loads applied to the spine (see FIG. 3c). The dynamic spine stabilization device 10 assists the compromised (injured and/or degenerated) spine of a back pain patient, and helps her/him perform daily activities. The dynamic spine stabilization device 10 does so by providing controlled resistance to spinal motion particularly around neutral posture in the region of neutral zone. As the spine bends forward (flexion) the stabilization device 10 is tensioned (see FIG. 3d) and when the spine bends backward (extension) the stabilization device 10 is compressed (see FIG. 3e).

The resistance to displacement provided by the dynamic spine stabilization device 10 is non-linear, being greatest in its central zone so as to correspond to the individual's neutral zone; that is, the central zone of the stabilization device 10 provides a high level of mechanical assistance in supporting the spine. As the individual moves beyond the neutral zone, the increase in resistance decreases to a more moderate level. As a result, the individual encounters greater resistance to movement (or greater incremental resistance) while moving within the neutral zone.

The central zone of the dynamic spine stabilization device 10, that is, the range of motion in which the spine stabilization device 10 provides the greatest resistance to movement, may be adjustable at the time of surgery to suit the neutral zone of each individual patient. In such exemplary embodiments, the resistance to movement provided by the dynamic spine stabilization device 10 is adjustable pre-operatively and intra-operatively. This helps to tailor the mechanical properties of the dynamic spine stabilization device 10 to suit the compromised spine of the individual patient. The length of the dynamic spine stabilization device 10 may also be adjustable intra-operatively to suit individual patient anatomy and to achieve desired spinal posture. The dynamic spine stabilization device 10 can be re-adjusted post-operatively with a surgical procedure to adjust its central zone to accommodate a patient's altered needs.

According to exemplary embodiments of the present disclosure, ball joints 20, 22 link the dynamic spine stabilization device 10 with the pedicle screws 16, 18. The junction of the dynamic spine stabilization device 10 and pedicle screws 16, 18 is free and rotationally unconstrained. Therefore, first of all, the spine is allowed all physiological motions of bending and twisting and second, the dynamic spine stabilization device 10 and the pedicle screws 16, 18 are protected from harmful bending and torsional forces, or moments. While ball joints are disclosed in accordance with a preferred/exemplary embodiment of the present disclosure, other linking structures may be utilized without departing from the spirit or scope of the present disclosure.

As there are ball joints 20, 22 at each end of the stabilization device 10, no bending moments can be transferred from the spine to the stabilization device 10. Further, it is important to recognize the only forces that act on the stabilization device 10 are those due to the forces of the springs 30, 32 within it.

These forces are solely dependent upon the tension and compression of the stabilizer 10 as determined by the spinal motion. In summary, the stabilization device 10 sees only the spring forces. Irrespective of the large loads on the spine, such as when a person carries or lifts a heavy load, the loads coming to the stabilization device 10 are only the forces developed within the stabilization device 10, which are the result of spinal motion and not the result of the spinal load. The stabilization device 10 is, therefore, uniquely able to assist the spine without enduring the high loads of the spine, allowing a wide range of design options.

The loading of the pedicle screws 16, 18 in the present stabilization device 10 is also quite different from that in prior art pedicle screw fixation devices. The only load the stabilizer pedicle screws 16, 18 see is the force from the stabilization device 10. This translates into pure axial force at the ball joint-screw interface. This mechanism greatly reduces the bending moment placed onto the pedicle screws 16, 18 as compared to prior art pedicle screw fusion systems. Due to the ball joints 20, 22, the bending moment within the pedicle screws 16, 18 is essentially zero at the ball joints 20, 22 and it increases toward the tip of the pedicle screws 16, 18. The area of pedicle screw-bone interface which often is the failure site in a typical prior art pedicle screw fixation device, is the least stressed site, and is therefore not likely to fail. In sum, the pedicle screws 16, 18, when used in conjunction with the present invention, carry significantly less load and are placed under significantly less stress than typical pedicle screws.

Figure 1:
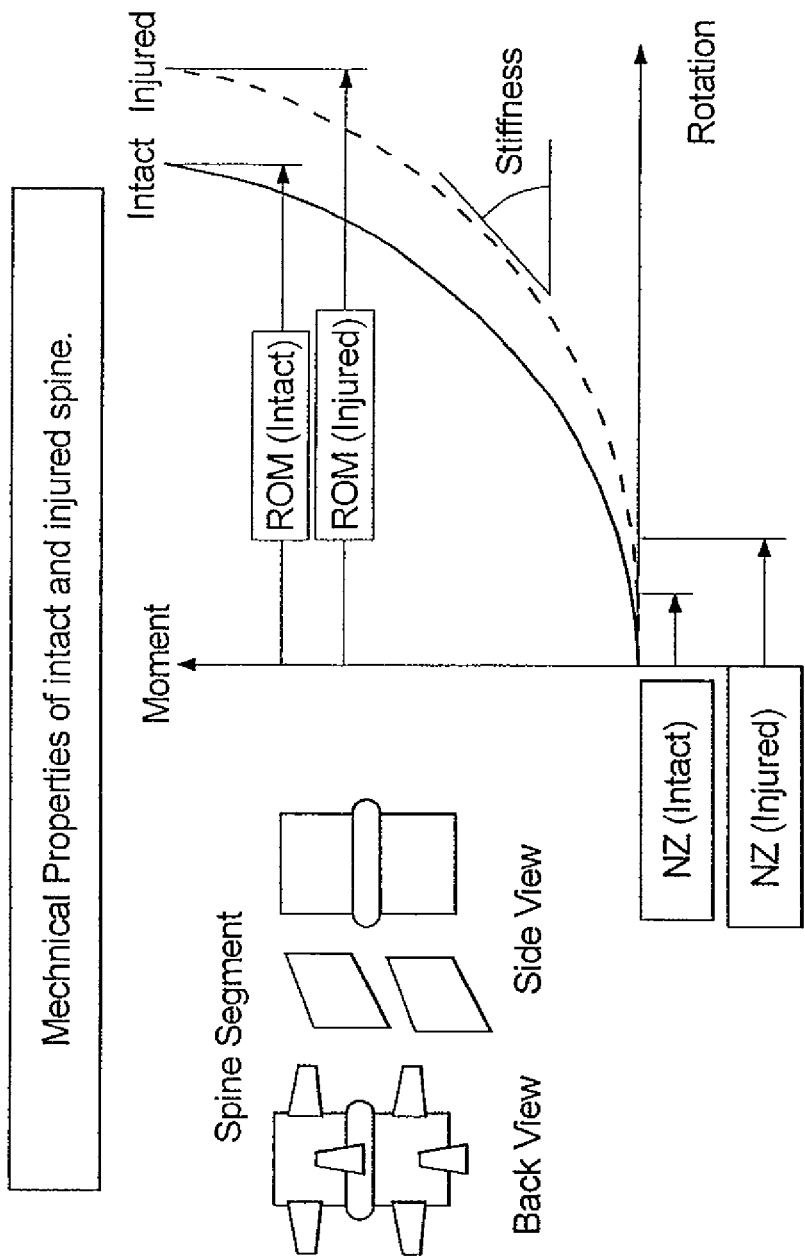
FIG. 1 is Moment-Rotation curve for a spinal segment (intact and injured), showing low spinal stiffness within the neutral zone.

In FIG. 2, the Moment-Rotation curve for a healthy spine is shown in configurations with stabilization device 10. This curve shows the low resistance to movement encountered in the neutral zone of a healthy spine. However, when the spine is injured, this curve changes and the spine becomes unstable, as evidenced by the expansion of the neutral zone (see FIG. 1).

In accordance with a preferred embodiment of the present invention, people suffering from spinal injuries are best treated through the application of increased mechanical assistance in the neutral zone. As the spine moves beyond the neutral zone, the necessary mechanical assistance decreases and becomes more moderate. In particular, and with reference to FIG. 3a, the support profile contemplated in accordance with the present invention is disclosed.

Figure 3A:
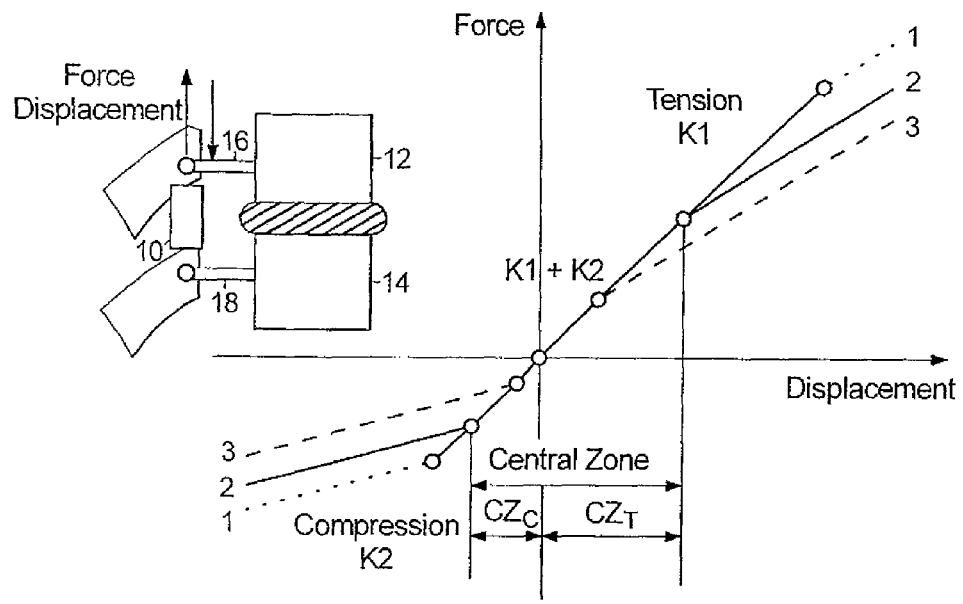
FIG. 3a is a schematic of a spinal stabilization device in conjunction with a Force-Displacement curve, demonstrating the increased resistance provided within the central zone according to spinal stabilization systems wherein a dynamic element is positioned between laterally-spaced pedicle screws.
Figure 3B:
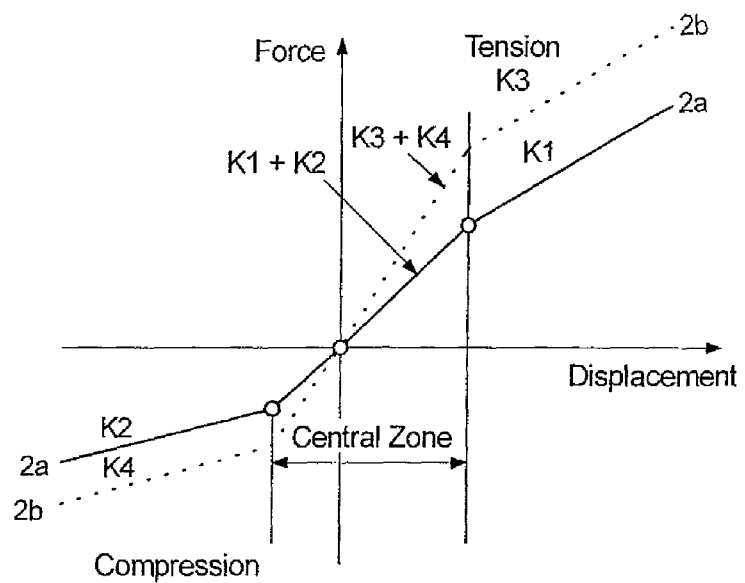
FIG. 3b is a Force-Displacement curve demonstrating the change in profile achieved through spring replacement.

Three different profiles are shown in FIG. 3a. The disclosed profiles are merely exemplary and demonstrate the possible support requirements within the neutral zone. Profile 1 is exemplary of an individual requiring great assistance in the neutral zone and the central zone of the stabilizer is therefore increased providing a high level of resistance over a great displacement; Profile 2 is exemplary of an individual where less assistance is required in the neutral zone and the central zone of the stabilizer is therefore more moderate providing increased resistance over a more limited range of displacement; and Profile 3 is exemplary of situations where only slightly greater assistance is required in the neutral zone and the central zone of the stabilizer may therefore be decreased to provide increased resistance over even a smaller range of displacement.

As those skilled in the art will certainly appreciate, the mechanical assistance required and the range of the neutral zone will vary from individual to individual. However, the basic tenet of the present invention remains; that is, greater mechanical assistance for those individuals suffering from spinal instability is required within the individual's neutral zone. This assistance is provided in the form of greater resistance to movement provided within the neutral zone of the individual and the central zone of the dynamic spine stabilizer 10.

The dynamic spine stabilization device 10 provides mechanical assistance in accordance with the disclosed support profile. Further, the stabilization device 10 may advantageously provide for adjustability via a concentric spring design.

More specifically, the dynamic spine stabilization device 10 provides assistance to the compromised spine in the form of increased resistance to movement (provided by springs in accordance with a preferred embodiment) as the spine moves from the neutral posture, in any physiological direction. As mentioned above, the Force-Displacement relationship provided by the dynamic spine stabilization device 10 is non-linear, with greater incremental resistance around the neutral zone of the spine and central zone of the stabilization device 10, and decreasing incremental resistance beyond the central zone of the dynamic spine stabilization device 10 as the individual moves beyond the neutral zone (see FIG. 3a).

The relationship of stabilization device 10 to forces applied during tension and compression is further shown with reference to FIG. 3a. As discussed above, the behavior of the stabilization device 10 is non-linear. The Load-Displacement curve has three zones: tension, central and compression. If K1 and K2 define the stiffness values in the tension and compression zones respectively, the present stabilizer is designed such that the high stiffness in the central zone is "K1+K2". Depending upon the preload of the stabilization device 10 as will be discussed below in greater detail, the width of the central zone and, therefore, the region of high stiffness can be adjusted.

Figure 4:
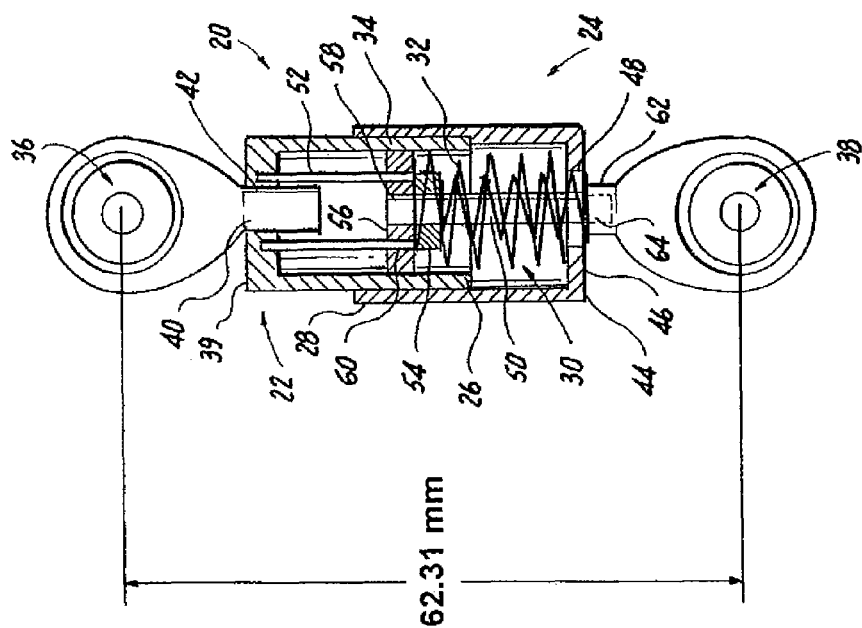
FIG. 4 is a schematic of a dynamic spine stabilization device that is adapted to position dynamic elements between laterally-spaced pedicle screws.

With reference to FIG. 4, a dynamic spine stabilization device 10 in accordance with one aspect of the present disclosure is schematically depicted. The dynamic spine stabilization device 10 includes a support assembly in the form of a housing 20 composed of a first housing member 22 and a second housing member 24. The first housing member 22 and the second housing member 24 are telescopically connected via external threads formed upon the open end 26 of the first housing member 22 and internal threads formed upon the open end 28 of the second housing member 24. In this way, the housing 20 is completed by screwing the first housing member 22 into the second housing member 24. As such, and as will be discussed below in greater detail, the relative distance between the first housing member 22 and the second housing member 24 can be readily adjusted for the purpose of adjusting the compression of the first spring 30 and second spring 32 contained within the housing 20. Although springs are employed in accordance with a preferred embodiment of the present disclosure, other elastic members may be employed without departing from the spirit or scope of the present disclosure. A piston assembly 34 links the first spring 30 and the second spring 32 to first and second ball joints 36, 38. The first and second ball joints 36, 38 are in turn shaped and designed for selective attachment to pedicle screws 16, 18 extending from the respective vertebrae 12, 14.

The first ball joint 36 is secured to the closed end 38 of the first housing member 20 via a threaded engagement member 40 shaped and dimensioned for coupling, with threads formed within an aperture 42 formed in the closed end 38 of the first housing member 22. In this way, the first ball joint 36 substantially closes off the closed end 38 of the first housing member 22. The length of the dynamic spine stabilization device 10 may be readily adjusted by rotating the first ball joint 36 to adjust the extent of overlap between the first housing member 22 and the engagement member 40 of the first ball joint 36. As those skilled in the art will certainly appreciate, a threaded engagement between the first housing member 22 and the engagement member 40 of the first ball joint 36 is disclosed in accordance with a preferred embodiment, although other coupling structures may be employed without departing from the spirit or scope of the present disclosure.

The closed end 44 of the second housing member 24 is provided with a cap 46 having an aperture 48 formed therein. As will be discussed below in greater detail, the aperture 48 is shaped and dimensioned for the passage of a piston rod 50 from the piston assembly 34 therethrough.

The piston assembly 34 includes a piston rod 50; first and second springs 30, 32; and retaining rods 52. The piston rod 50 includes a stop nut 54 and an enlarged head 56 at its first end 58. The enlarged head 56 is rigidly connected to the piston rod 50 and includes guide holes 60 through which the retaining rods 52 extend during operation of dynamic spine stabilization device 10. As such, the enlarged head 56 is guided along the retaining rods 52 while the second ball joint 38 is moved toward and away from the first ball joint 36. As will be discussed below in greater detail, the enlarged head 56 interacts with the first spring 30 to create resistance as the dynamic spine stabilization device 10 is extended and the spine is moved in flexion.

A stop nut 54 is fit over the piston rod 50 for free movement relative thereto. However, movement of the stop nut 54 toward the first ball joint 36 is prevented by the retaining rods 52 that support the stop nut 54 and prevent the stop nut 54 from moving toward the first ball joint 36. As will be discussed below in greater detail, the stop nut 54 interacts with the second spring 32 to create resistance as the dynamic spine stabilizer 10 is compressed and the spine is moved in extension.

The second end 62 of the piston rod 50 extends from the aperture 48 at the closed end 44 of the second housing member 24, and is attached to an engagement member 64 of the second ball joint 38. The second end 62 of the piston rod 50 is coupled to the engagement member 64 of the second ball joint 38 via a threaded engagement. As those skilled in the art will certainly appreciate, a threaded engagement between the second end 62 of the piston rod 50 and the engagement member 64 of the second ball joint 38 is disclosed in accordance with a preferred embodiment, although other coupling structures may be employed without departing from the spirit of the present invention.

As briefly mentioned above, the first and second springs 30, 32 are held within the housing 20. In particular, the first spring 30 extends between the enlarged head 56 of the piston rod 50 and the cap 46 of the second housing member 24. The second spring 32 extends between the distal end of the engagement member 64 of the second ball joint 38 and the stop nut 54 of the piston rod 50. The preloaded force applied by the first and second springs 30, 32 holds the piston rod in a static position within the housing 20, such that the piston rod is able to move during either extension or flexion of the spine.

In use, when the vertebrae 12, 14 are moved in flexion and the first ball joint 36 is drawn away from the second ball joint 38, the piston rod 50 is pulled within the housing 24 against the force being applied by the first spring 30. In particular, the enlarged head 56 of the piston rod 50 is moved toward the closed end 44 of the second housing member 24. This movement causes compression of the first spring 30, creating resistance to the movement of the spine. With regard to the second spring 32, the second spring 32 moves with the piston rod 50 away from second ball joint 38. As the vertebrae move in flexion within the neutral zone, the height of the second spring 32 is increased, reducing the distractive force, and in effect increasing the resistance of the device to movement. Through this mechanism, as the spine moves in flexion from the initial position both spring 30 and spring 32 resist the distraction of the device directly, either by increasing the load within the spring (i.e. first spring 30) or by decreasing the load assisting the motion (i.e. second spring 32).

However, when the spine is in extension, and the second ball joint 38 is moved toward the first ball joint 36, the engagement member 64 of the second ball joint 38 moves toward the stop nut 54, which is held is place by the retaining rods 52 as the piston rod 50 moves toward the first ball joint 36. This movement causes compression of the second spring 32 held between the engagement member 64 of the second ball joint 38 and the stop nut 54, to create resistance to the movement of the dynamic spine stabilization device 10. With regard to the first spring 30, the first spring 30 is supported between the cap 46 and the enlarged head 56, and as the vertebrae move in extension within the neutral zone, the height of the second spring 30 is increased, reducing the compressive force, and in effect increasing the resistance of the device to movement. Through this mechanism, as the spine moves in extension from the initial position both spring 32 and spring 30 resist the compression of the device directly, either by increasing the load within the spring (i.e. second spring 32) or by decreasing the load assisting the motion (i.e. first spring 30).

Based upon the use of two concentrically positioned elastic springs 30, 32 as disclosed in accordance with the present disclosure, an assistance (force) profile as shown in FIG. 2 is provided by the present dynamic spine stabilizer 10. That is, the first and second springs 30, 32 work in conjunction to provide a large elastic force when the dynamic spine stabilization device 10 is displaced within the central zone. However, once displacement between the first ball joint 36 and the second ball joint 38 extends beyond the central zone of the stabilization device 10 and the neutral zone of the individual's spinal movement, the incremental resistance to motion is substantially reduced as the individual no longer requires the substantial assistance needed within the neutral zone. This is accomplished by setting the central zone of the device disclosed herein. The central zone of the force displacement curve is the area of the curve which represents when both springs are acting in the device as described above. When the motion of the spine is outside the neutral zone and the correlating device elongation or compression is outside the set central zone, the spring which is elongating reaches its free length. Free length, as anybody skilled in the art will appreciate, is the length of a spring when no force is applied. In this mechanism the resistance to movement of the device outside the central zone (where both springs are acting to resist motion) is only reliant on the resistance of one spring: either spring 30 in flexion or spring 32 in extension.

As briefly discussed above, dynamic spine stabilization device 10 may be adjusted by rotation of the first housing member 22 relative to the second housing member 24. This movement changes the distance between the first housing member 22 and the second housing member 24 in a manner which ultimately changes the preload placed across the first and second springs 30, 32. This change in preload alters the resistance profile of the present dynamic spine stabilization device 10 from that shown in Profile 2 of FIG. 3a to an increase in preload (see Profile 1 of FIG. 3a) which enlarges the effective range in which the first and second springs 30, 32 act in unison. This increased width of the central zone of the stabilization device 10 correlates to higher stiffness over a larger range of motion of the spine. This effect can be reversed as evident in Profile 3 of FIG. 3a.

The dynamic spine stabilization device 10 is attached to pedicle screws 16, 18 extending from the vertebral section requiring support. During surgical attachment of the dynamic spine stabilization device 10, the magnitude of the stabilizer's central zone can be adjusted for each individual patient, as judged by the surgeon and/or quantified by an instability measurement device. This optional adjustable feature of dynamic spine stabilization device 10 is exemplified in the three explanatory profiles that have been generated in accordance with the present disclosure (see FIG. 2; note the width of the device central zones).

Pre-operatively, the first and second elastic springs 30, 32 of the dynamic spine stabilization device 10 can be replaced by a different set to accommodate a wider range of spinal instabilities. As expressed in FIG. 3b, Profile 2b demonstrates the force displacement curve generated with a stiffer set of springs when compared with the curve shown in Profile 2a of FIG. 3b.

Intra-operatively, the length of the dynamic spine stabilization device 10 is adjustable by turning the engagement member 40 of the first ball joint 36 to lengthen the stabilization device 10 in order to accommodate different patient anatomies and desired spinal posture. Pre-operatively; the piston rod 50 may be replaced to accommodate an even wider range of anatomic variation.

The dynamic spine stabilization device 10 has been tested alone for its load-displacement relationship. When applying tension, the dynamic spine stabilization device 10 demonstrated increasing resistance up to a pre-defined displacement, followed by a reduced rate of increasing resistance until the device reached its fully elongated position. When subjected to compression, the dynamic spine stabilization device 10 demonstrated increasing resistance up to a pre-defined displacement, followed by a reduced rate of increasing resistance until the device reached its fully compressed position. Therefore, the dynamic spine stabilization device 10 exhibits a load-displacement curve that is non-linear with the greatest resistance to displacement offered around the neutral posture. This behavior helps to normalize the load-displacement curve of a compromised spine.

Figure 5:
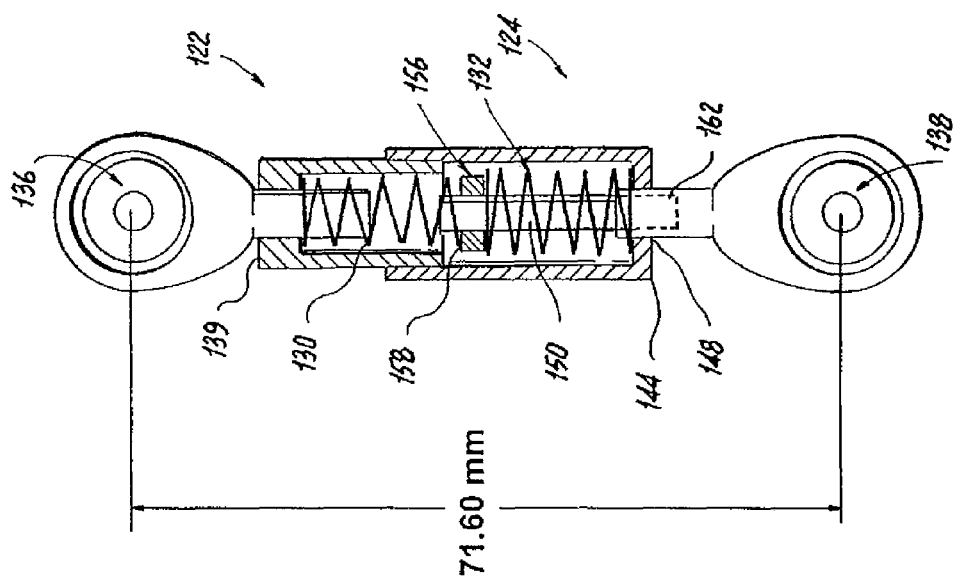
FIG. 5 is a schematic of an alternate dynamic spine stabilization device that is adapted to position dynamic elements between laterally-spaced pedicle screws.

In another embodiment of an aspect of the disclosed design and with reference to FIG. 5, the stabilization device 110 may be constructed with an in-line spring arrangement. In accordance with this embodiment, the housing 120 is composed of first and second housing members 122, 124 which are coupled with threads allowing for adjustability. A first ball joint 136 extends from the first housing member 122. The second housing member 124 is provided with an aperture 148 through which the second end 162 of piston rod 150 extends. The second end 162 of the piston rod 150 is attached to the second ball joint 138. The second ball joint 138 is screwed onto the piston rod 150.

The piston rod 150 includes an enlarged head 156 at its first end 158. The first and second springs 130, 132 are respectively secured between the enlarged head 156 and the closed ends 138, 144 of the first and second housing members 122, 124. In this way, the stabilization device 110 provides resistance to both expansion and compression using the same mechanical principles described for the previous embodiment.

Adjustment of the resistance profile in accordance with this alternate embodiment is achieved by rotating the first housing member 122 relative to the second housing member 124. Rotation in this way alters the central zone of high resistance provided by the stabilization device 110. As previously described one or both springs may also be exchanged to change the slope of the force-displacement curve in two or three zones respectively.

Figure 6:
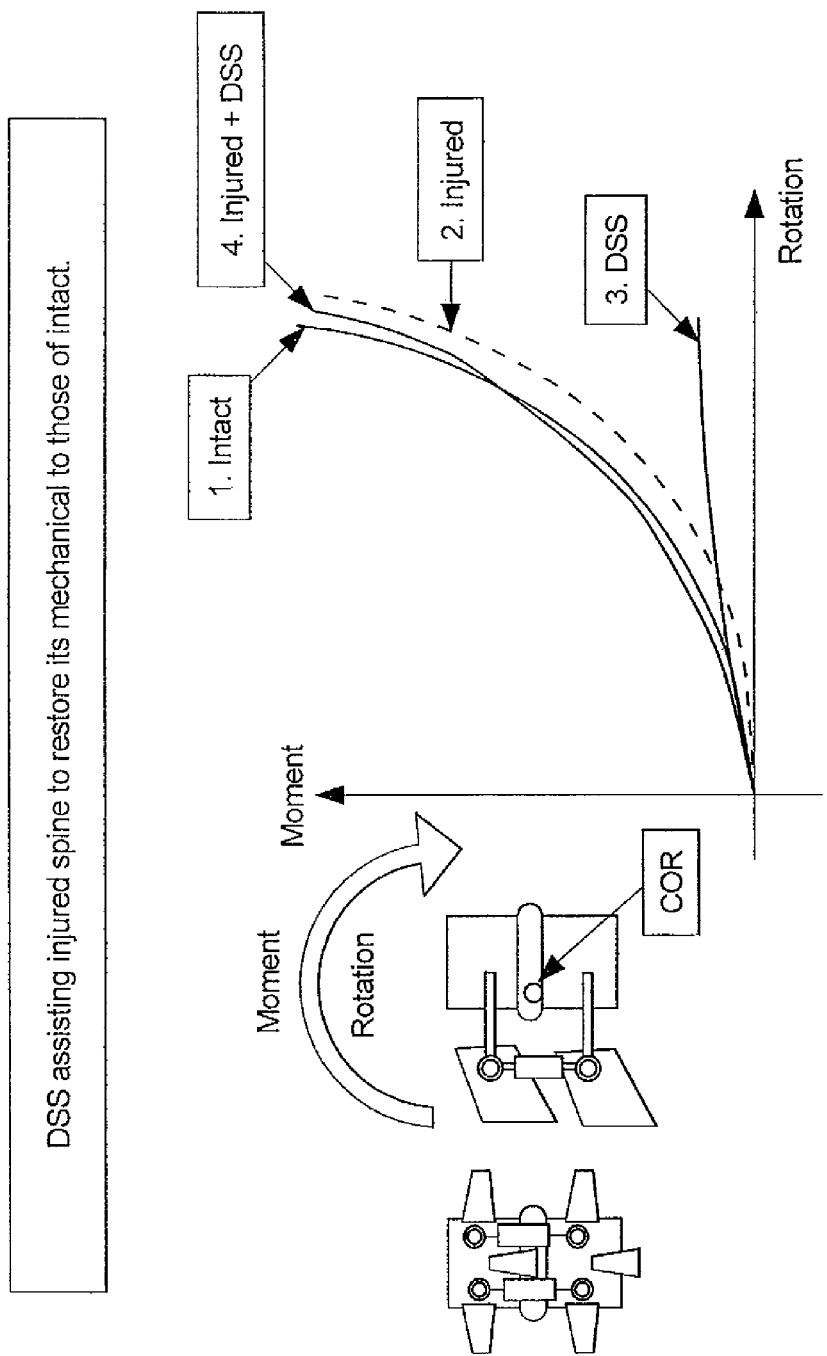
FIG. 6 is a Moment-Rotation curve demonstrating the manner in which dynamic stabilization devices using the principles of the present disclosure assist in spinal stabilization.

To explain how the stabilization device 10, 110 assists a compromised spine (increased neutral zone), reference is made to the moment-rotation curves (FIG. 6). Four curves are shown: 1. Intact, 2. Injured, 3. Stabilizer and, 4. Injured+Stabilizer. These are, respectively, the Moment-Rotation curves of the intact spine, injured spine, stabilizer alone, and stabilizer plus injured spine Notice that this curve is close to the intact curve. Thus, the stabilization device, which provides greater resistance to movement around the neutral posture, is ideally suited to compensate for the instability of the spine.

With reference to FIGS. 8 to 13, a stabilization device 210 according to the present disclosure is schematically depicted. This embodiment positions the first and second springs 230, 232 on opposite sides of a pedicle screw 218. As with the earlier embodiments, the stabilization device 210 includes a housing 220 having a first attachment member 260 with a first ball joint 262 extending from a first end 264 of the housing 220 and a second attachment member 266 with second ball joint 268 extending through a central portion of the stabilizer 220. Each of the ball joints 262, 268 is composed of a socket 270a, 270b with a ball 272a, 272b secured therein.

More particularly, each of the pedicle screws 216, 218 includes a proximal end 274 and a distal end 276 (as the first and second pedicle screws 216, 218 are identical, similar numerals will be used in describing them). The proximal end 274 includes traditional threading 278 adapted for secure attachment along the spinal column of an individual. The distal end 276 of the pedicle screw 216, 218 is provided with a collet 278 adapted for engagement within a receiving aperture 280a, 280b formed within the ball 272a, 272b of the first and second attachment members 260, 266 of the stabilization device 210.

The collet 278 at the distal end 276 of the pedicle screw 216, 218 is formed with the ability to expand and contract under the control of the medical practitioner installing the present stabilizer 210. The collet 278 is composed of a plurality of flexible segments 282 with a central aperture 284 therebetween. As will be explained below in greater detail, the flexible segments 282 are adapted for movement between an expanded state used to lock the collet 278 within the receiving aperture 280a, 280b of the ball 272a, 272b and an unexpanded state wherein the collet 278 may be selectively inserted or removed from the receiving aperture 280a, 280b of the ball 272a, 272b.

The receiving apertures 280a, 280b of the respective balls 272a, 272b are shaped and dimensioned for receiving the collet 278 of the pedicle screw 216, 218 while it is in its unexpanded state. Retention of the collet 278 is further enhanced by the provision of a lip 286 at the distal end 276 of the collet 278. The lip 286 is shaped and dimensioned to grip the receiving aperture 280a, 280b for retaining the collet 278 therein.

Expansion of the collet 278 of pedicle screw 216, 218 is achieved by the insertion of a set screw 288 within the central aperture 284 formed between the various segments 282 of the pedicle screw collet 278. As the set screw 288 is positioned within the central aperture 284, the segments 282 are forced outwardly. This increases the effective diameter of the collet 278 and ultimately brings the outer surface of the collet 278 into contact with the receiving aperture 280a, 280b, securely locking the collet 278, that is, the distal end 276 of the pedicle screw 216, 218 within the receiving aperture 280a, 280b of the ball 272a, 272b.

Access for the insertion of the set screw 288 within the central aperture 284 of the collet 278 is provided by extending the receiving aperture 280a, 280b the entire way through the ball 272a, 272b. In this way, the collet 278 is placed within the receiving aperture 280a, 280b of the ball 272a, 272b while in its unexpanded state, the set screw 288 is inserted within the central aperture 284 between the various segments 282 to cause the segments 282 to expand outwardly and lock the collet 278 within the receiving aperture 280a, 280b. In accordance with a preferred embodiment, the set screw 288 is secured within the central aperture 284 via mating threads formed along the inner surface along of the central aperture and the outer surface of the set screw 288.

Although the present ball joint/pedicle screw structure has been disclosed with reference to a particle stabilizer structure, those skilled in the art will appreciate that the ball joint/pedicle screw structure may be employed with various stabilizer structures without departing from the spirit of the present invention. In fact, it is contemplated the disclosed connection structure may be employed in a variety of environments without departing from the spirit of the present invention.

With reference to the stabilization device 210, an alignment pin 250 extends from the first attachment member 260 through a bearing aperture 290 within the second attachment member 266. The alignment pin 250 includes an abutment member 256 at its free end 258. First and second springs 230, 232 are concentrically positioned about the alignment pin 250. The first spring 230 is positioned to extend between the first attachment member 260 and the second attachment member 266, while the second spring 232 is positioned to extend between the second attachment member 266 and the abutment member 256 at the free end 258 of the alignment pin 250. The arrangement of the alignment pin 250, first and second attachment members 260, 266 and first and second springs 230, 232 allows for resistive translation of the alignment pin 250 relative to the vertebrae. In practice, the alignment pin 250, springs 230, 232 and attachment members 260, 266 are arranged to create a compressive preload across the system.

This design allows for an axial configuration which generates the desired Force-Displacement curves as shown with reference to FIG. 3, while allowing for a much shorter distance between the first and second attachment members. The stabilization device disclosed above may also be used in the stabilization of multiple level systems. It is contemplated that stabilization on multiple levels may be achieved through the implementation of multiple alignment pins coupled via multiple spring sets and pedicle screws.

The alignment pin 250 also provides tensile force for achieving the preload utilized in conjunction with the springs 230, 232. In accordance with an exemplary embodiment, the alignment pin 250 is flexible and provides flexible guidance for the springs 230, 232 without debris causing bearing surfaces, provides tensile for the preload, provides a low friction, straight bearing surface as it moves through the second attachment member 266 and functions at times as a straight member and at other times as a flexible guide for springs 230, 232.

As mentioned above, the alignment pin 250 is cable of functioning as both a straight guide member and as a flexible guide member. The determination as to whether the alignment pin 250 functions as a straight guide member or a flexible guide member for the springs 230, 232 is generally based upon location of the alignment pin 250 relative to the remaining stabilization device 210 components as the spine moves. This functionality is especially important during flexion. In accordance with an exemplary embodiment, the alignment pin 250 has a uniform cross sectional shape capable of performing as both a straight guide member and a flexed guide member.

Figure 3C:
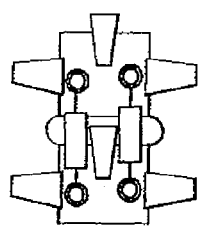
FIG. 3c is a dorsal view of the spine with a pair of dynamic stabilization devices secured thereto.
Figure 3D:
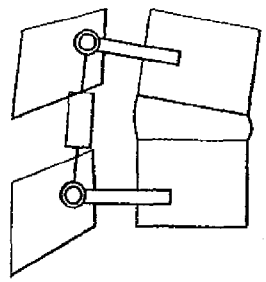
FIG. 3d is a side view showing the exemplary dynamic stabilization device in tension.
Figure 3E:
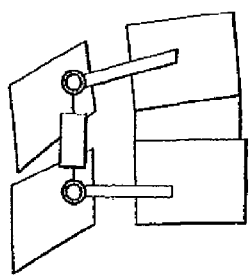
FIG. 3e is a side view showing the exemplary dynamic stabilization device in compression.
Figure 13:
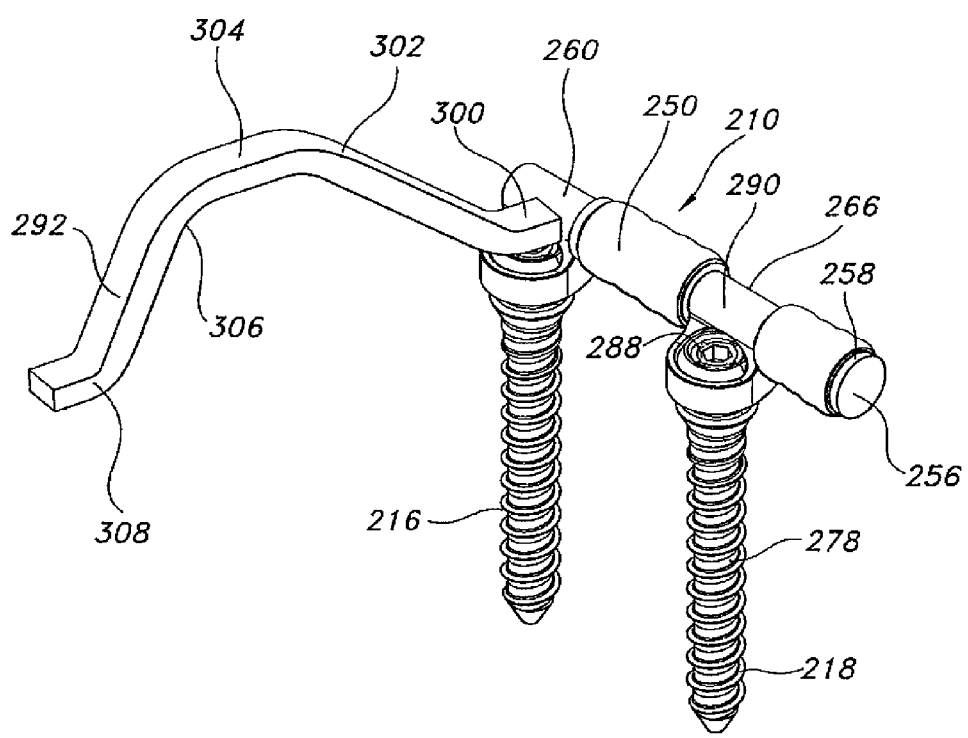
FIG. 13 is a perspective view of a dynamic stabilization device of the type depicted in FIG. 8 with a transverse torsion bar stabilizing member.

In accordance with yet a further embodiment, and with reference to FIG. 13, the stabilization device 210 may be used in conjunction with a torsion bar 292 connecting the stabilization device 210 to adjacent stabilizers as shown in FIG. 3c. In accordance with an exemplary embodiment, the torsion bar 292 is connected to the attachment members 260, 266 of adjacent stabilization devices with conventional connection structures. The use of the torsion bar 292 increases stability in axial rotation or lateral bending. The torsion bar 292 generally has a uniform cross section for purposes where uniform torsion is required. However, and in accordance with exemplary embodiments of the present disclosure, it is contemplated that the torsion bar 292 may have an asymmetric cross section so as to provide for flexibility of stiffness in two planes. In such instances, the asymmetric cross sectional torsion bar 292 will affect the system stiffness in lateral bending and axial rotation independently. Further, the torsion bar 292 may be utilized to tune the systems stabilization in all three planes.

Figure 14:
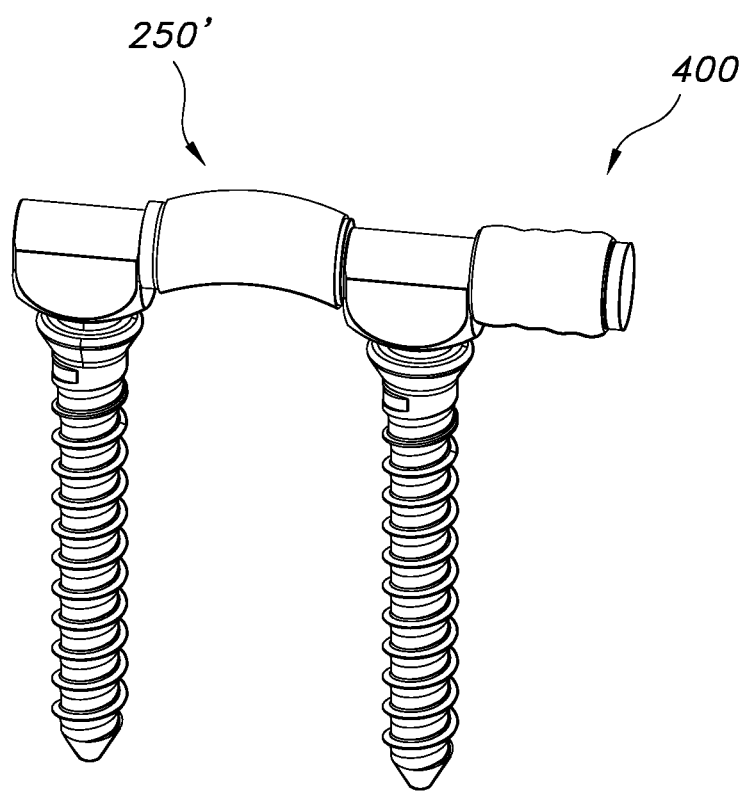
FIG. 14 is a perspective view of a further exemplary dynamic stabilization device according to the present disclosure.

With reference to FIG. 14, a further exemplary dynamic stabilization device 400 is provided wherein the elongate element 250' defines a travel path that includes at least one curved section.

In addition to the dynamic spine stabilization device described above, other complementary devices are contemplated. For example, a link-device may be provided for joining the left- and right-stabilizer units to help provide additional stability in axial rotation and lateral bending. This link-device would be a supplement to the dynamic spine stabilization device and would be applied as needed on an individual patient basis. In addition, a spinal stability measurement device may be utilized. The measurement device would be used to quantify the stability of each spinal level at the time of surgery. This device would attach intra-operatively to a pair of adjacent spinal components at compromised and uncompromised spinal levels to measure the stability of each level. The stability measurements of the adjacent uninjured levels relative to the injured level(s) can be used to determine the appropriate adjustment of the device. Additionally, the stability measurements of the injured spinal level(s) can be used to adjust the device by referring to a tabulated database of normal uninjured spinal stabilities. The device will be simple and robust, so that the surgeon is provided with the information in the simplest possible manner under operative conditions.

The choice of spring(s) to be used in accordance with the present disclosure to achieve the desired force profile curve is governed by the basic physical laws governing the force produced by springs. In particular, the force profile described above and shown in FIG. 3a is achieved through the unique design of the present stabilizer.

Figure 7A:
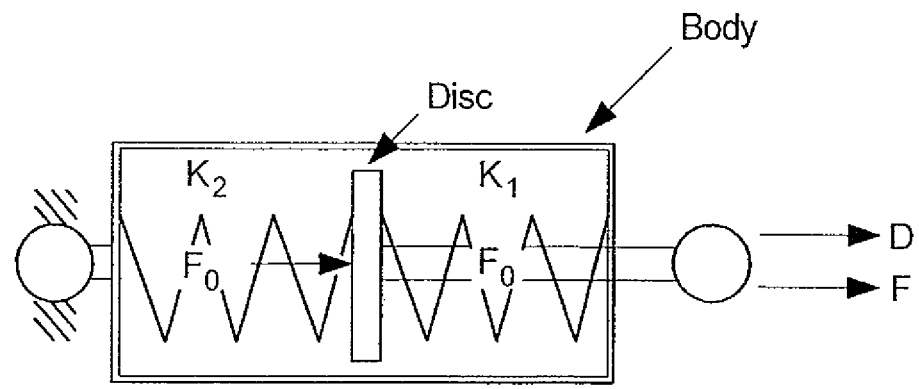
FIG. 7a is a free body diagram of a dynamic stabilization device in which dynamic elements are positioned between laterally-spaced pedicle screws.
Figure 7B:
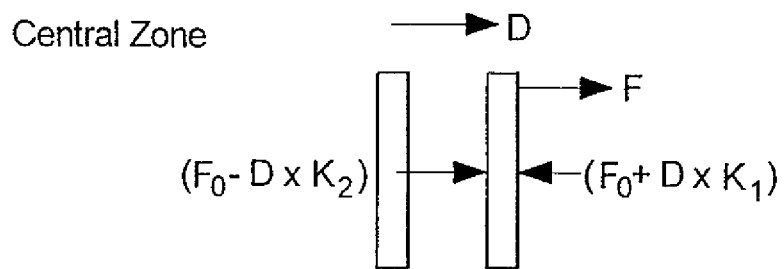
FIG. 7b is a diagram representing the central zone of a spine and the forces associated therewith for dynamic stabilization according to the present disclosure.
Figure 8:
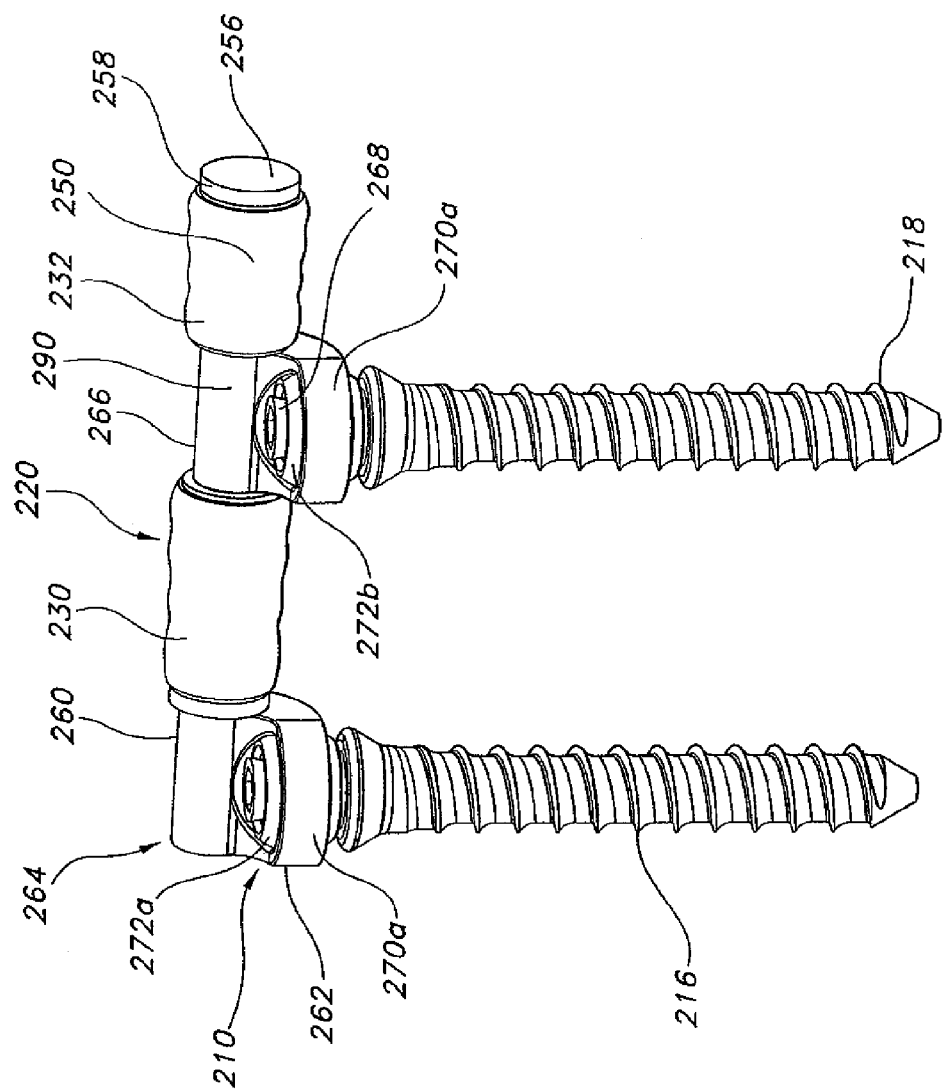
FIG. 8 is a perspective view of an exemplary dynamic stabilization device in accordance with the present disclosure.
Figure 9:
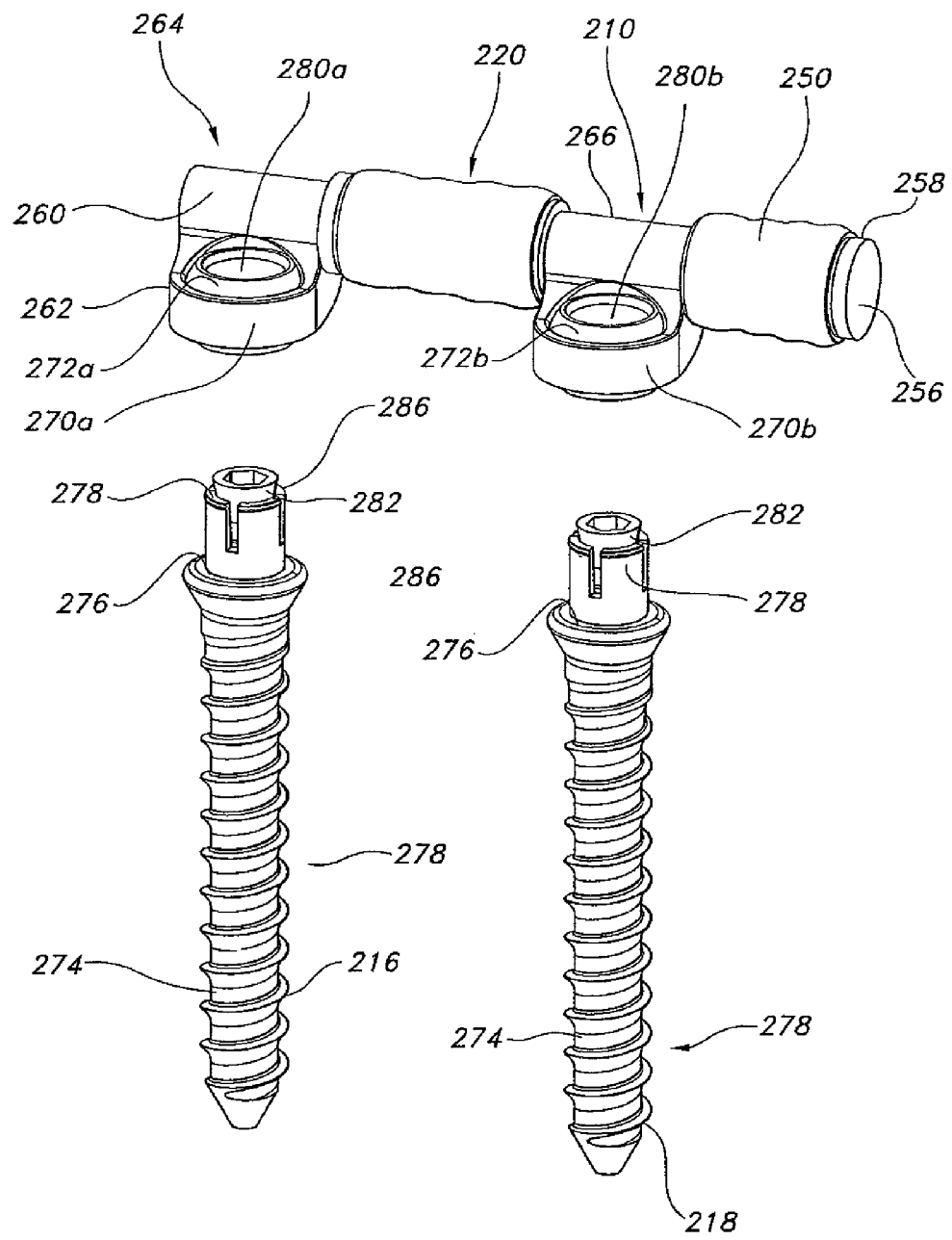
FIG. 9 is an exploded view of the dynamic stabilization device shown in FIG. 8.
Figure 10:
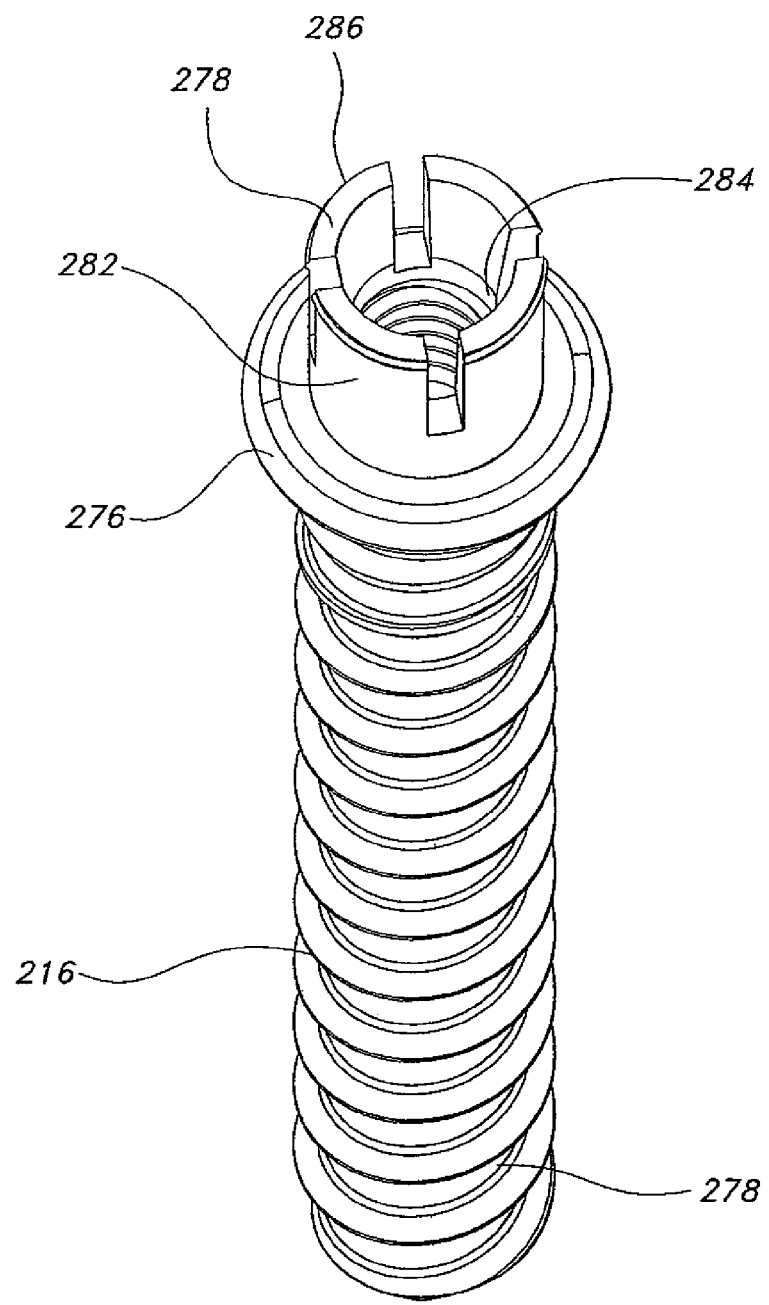
FIG. 10 is a detailed perspective view of the distal end of a first pedicle screw for use in exemplary implementations of the present disclosure; according to exemplary embodiments of the present disclosure, the second pedicle screw is identical.
Figure 11:
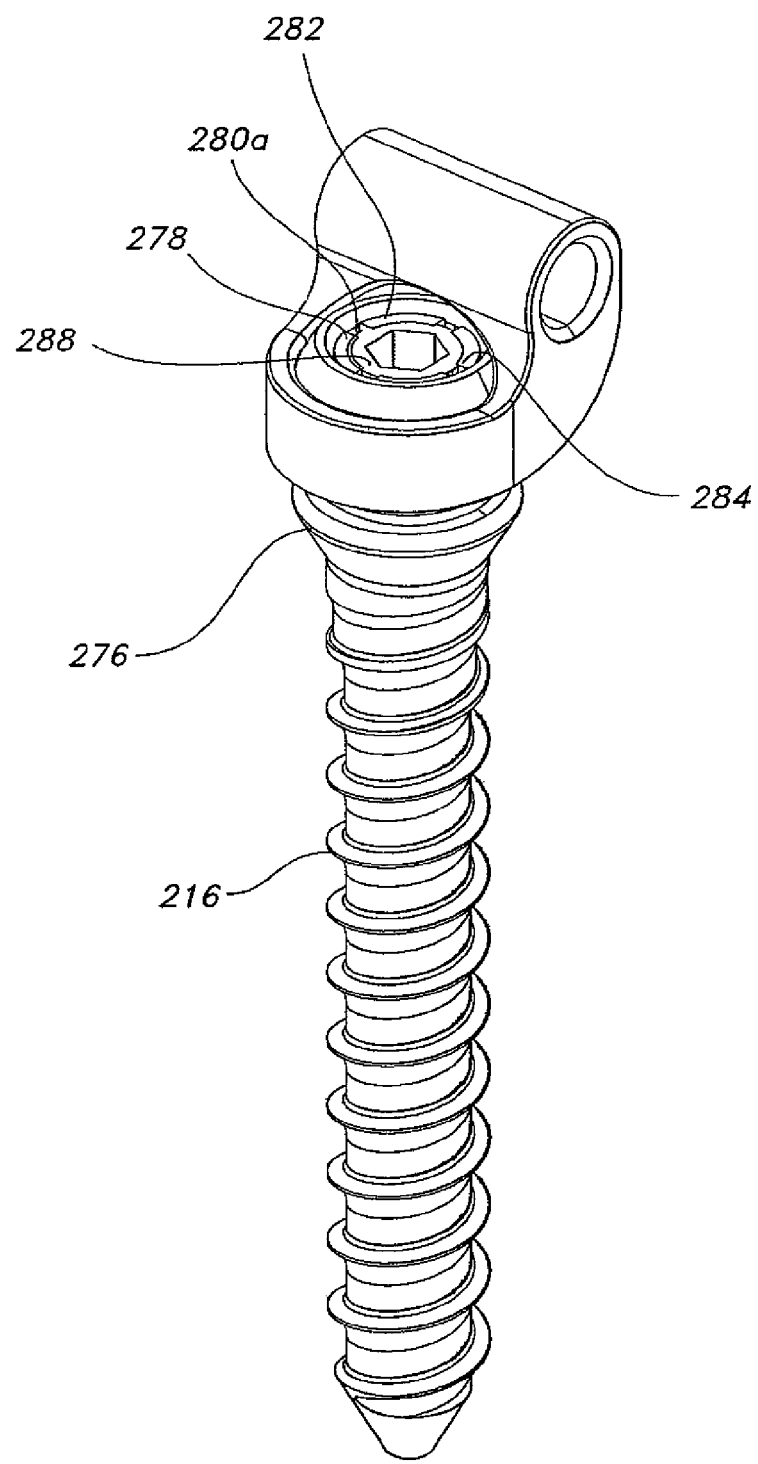
FIG. 11 is a detailed perspective view of a first pedicle screw secured to an exemplary attachment member according to the present disclosure.
Figure 12:
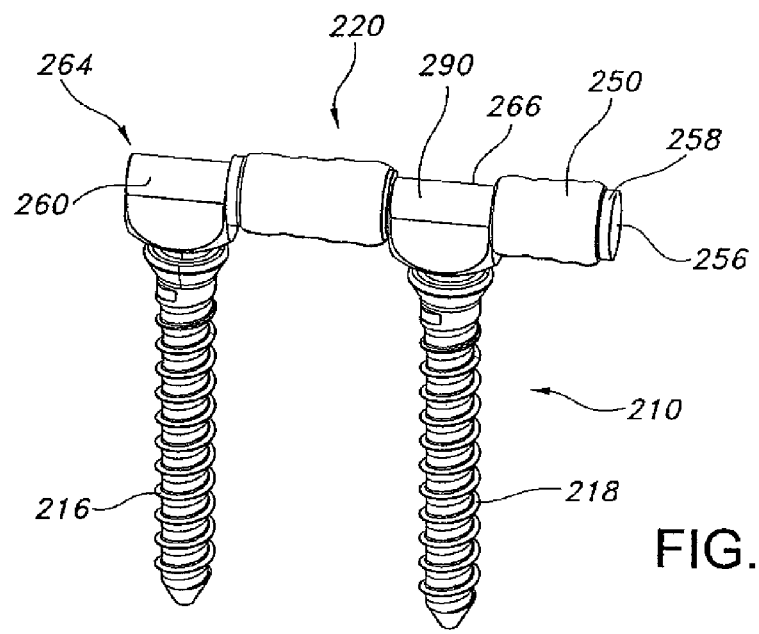
FIG. 12 is a perspective view of the exemplary dynamic stabilization device shown in FIG. 8 as seen from the opposite side.

First, the stabilization device functions both in compression and tension, even through the two springs within the stabilizer are both of compression type. Second, the higher stiffness ($K_1+K_2$) provided by the stabilization device in the central zone is due to the presence of a preload. Both springs are made to work together, when the preload is present. As the stabilization device is either tensioned or compressed, the force increases in one spring and decreases in the other. When the decreasing force reaches the zero value, the spring corresponding to this force no longer functions, thus decreasing the stabilization device function, an engineering analysis, including the diagrams shown in FIGS. 7a and 7b, is presented below (the analysis specifically relates to the embodiment disclosed in FIG. 5, although those skilled in the art will appreciate the way in which it applies to all embodiments disclosed in accordance with the present invention).

$F_0$ is the preload within the stabilization device, introduced by shortening the body length of the housing as discussed above.

$K_1$ and $K_2$ are stiffness coefficients of the compression springs, active during stabilization device tensioning and compression, respectively.

F and D are respectively the force and displacement of the disc of the stabilization device with respect to the body of the stabilizer.

The sum of forces on the disc must equal zero. Therefore, $$F+(F_0-D\times K_2)-(F_0+D\times K_1)=0, \text{ and}$$

$$F=D\times(K_1+K_2).$$

With regard to the central zone (CZ) width (see FIG. 3a):
On Tension side $CZ_T$ is:

$$CZ_T=F_0/K_2.$$

On Compression side CZc is:

$$CZ_c=F_0/K_1.$$

As those skilled in the art will certainly appreciate, the concepts underlying the present disclosure may be applied to other medical procedures. As such, these concepts may be utilized beyond spinal treatments without departing from the spirit or scope of the present invention.

While exemplary embodiments have been shown and described, it will be understood that there is no intent to limit the invention by such disclosure, but rather, is intended to cover all modifications and alternate constructions falling within the spirit and scope of the invention.

The invention claimed is:

1. A method of stabilizing a pair of adjacent spinal vertebrae, comprising the steps of:
implanting first and second pedicle screws to the adjacent spinal vertebrae; and
coupling a dynamic stabilization device with respect to said first and second pedicle screws, said dynamic stabilization device including an elongate element that defines an extension region that is bounded by (i) an attachment member associated with the first pedicle screw, and (ii) an abutment member associated with a free end of the elongate element,
wherein said dynamic stabilization device includes no more than two dynamic elements, a first dynamic element mounted with respect to said elongate element between said first and second pedicle screws so as to deliver non-torsional force with respect to the spinal vertebrae and a second dynamic element mounted with respect to said elongate element in the extension region so as to deliver non-torsional force with respect to the spinal vertebrae.

2. The stabilization method according to claim 1, further comprising positioning the attachment member with respect to the first pedicle screw.

3. The stabilization method according to claim 2, further comprising positioning a second attachment member with respect to the second pedicle, and wherein said dynamic stabilization device is coupled with respect to said first and second attachment members.

4. The stabilization method according to claim 1, wherein the elongate element defines an axis of travel, and wherein the attachment member assumes an intermediate position along the travel path.

5. The stabilization method according to claim 1, wherein the first and second dynamic elements simultaneously apply first and second urging forces with respect to the first and second pedicle screws.

6. The stabilization method according to claim 5, wherein the first and second urging forces have opposite orientations.

7. The stabilization method according to claim 1, wherein the first and second dynamic elements comprise axially-oriented springs.

8. The stabilization method according to claim 1, wherein the elongate element defines a travel path that is substantially straight.

9. The stabilization method according to claim 1, wherein the extension region of the elongate element is cantilevered relative to the attachment member.

10. The stabilization method according to claim 1, wherein (i) the stabilization device defines a first end and the free end spaced from said first end, (ii) the elongate element has an elongate aspect that extends from a position adjacent the first end and a position adjacent the free end; (iii) a stop is coupled with respect to the elongate element adjacent the first end; (iv) the abutment member is coupled with respect to the elongate element adjacent the free end; (v) the attachment member is positioned between the stop and the abutment member, and is movably coupled with respect to the elongate element; and (vi) the abutment member and the second dynamic element are cantilevered relative to the attachment member.

11. The stabilization method according to claim 10, wherein the stop is coupled to the second pedicle screw by way of a first dynamic junction assembly.

12. The stabilization method according to claim 10, wherein the attachment member is coupled to the first pedicle screw by way of a second dynamic junction assembly.

13. The stabilization method according to claim 10, wherein the stabilization device delivers a non-linear force displacement response relative to the stop and the attachment member, the non-linear displacement response being characterized by a first force displacement curve in proximity to a central zone of the spine, a second displacement curve associated with tension of the spine removed from said central zone that differs from said first force displacement curve, and a third displacement curve associated with compression of the spine removed from said central zone that also differs from said first displacement curve.

14. A method of stabilizing a pair of adjacent spinal vertebrae, comprising the steps of:
implanting first and second pedicle screws to the adjacent spinal vertebrae; and
coupling a dynamic stabilization device with respect to said first and second pedicle screws, said dynamic stabilization device including an elongate element that defines an extension region that is bounded by (i) an attachment member associated with the first pedicle screw, and (ii) an abutment member associated with a free end of the elongate element,
wherein said dynamic stabilization device includes a first dynamic element mounted with respect to said elongate element between said first and second pedicle screws and a second dynamic element mounted with respect to said elongate element in the extension region; and
wherein said first and second dynamic elements simultaneously apply first and second urging forces with respect to the first and second pedicle screws that have opposite orientations; and wherein the first dynamic element and the second dynamic element are each mounted with respect to the elongate element so as to deliver non-torsional force with respect to the spinal vertebrae.

* * * * *